(12) United States Patent
Schwartz et al.

(10) Patent No.: US 8,070,485 B2
(45) Date of Patent: Dec. 6, 2011

(54) NOTCHED PONTIC AND SYSTEM FOR FABRICATING DENTAL APPLIANCE FOR USE THEREWITH

(75) Inventors: Dann A. Schwartz, Kenner, LA (US); John J. Sheridan, Metairie, LA (US)

(73) Assignee: Dentsply International, Inc., York, PA (US)

( * ) Notice: Subject to any disclaimer, the term of this patent is extended or adjusted under 35 U.S.C. 154(b) by 0 days.

(21) Appl. No.: 12/386,682

(22) Filed: Apr. 22, 2009

(65) Prior Publication Data

US 2009/0208908 A1 Aug. 20, 2009

(51) Int. Cl.
*A61C 3/00* (2006.01)

(52) U.S. Cl. .............................. 433/6; 433/24

(58) Field of Classification Search ............... 433/6, 167, 433/168.1, 171, 34, 202.1, 3, 24, 169, 170, 433/172, 223, 218; 264/19, 20, 16–18
See application file for complete search history.

(56) References Cited

U.S. PATENT DOCUMENTS

| | | | |
|---|---|---|---|
| 3,574,941 A | 4/1971 | Ritter | |
| 3,682,571 A | 8/1972 | Greenberg et al. | |
| 3,724,075 A | 4/1973 | Kesling | |
| 4,080,736 A | 3/1978 | Kennedy | |
| 4,676,745 A | 6/1987 | Zurita | |
| 4,957,439 A | 9/1990 | Shoher et al. | |
| 4,959,014 A | 9/1990 | Sheridan | |
| 5,044,951 A | 9/1991 | Sheridan | |
| 5,127,830 A | 7/1992 | Sheridan et al. | |
| 5,139,419 A | 8/1992 | Andreiko et al. | |
| 5,338,198 A | 8/1994 | Wu et al. | |
| 5,368,478 A | 11/1994 | Andreiko et al. | |
| 5,395,238 A | 3/1995 | Andreiko et al. | |
| 5,431,562 A | 7/1995 | Andreiko et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,464,349 A | 11/1995 | Andreiko et al. | |
| 5,474,448 A | 12/1995 | Andreiko et al. | |
| RE35,169 E | 3/1996 | Lemchen et al. | |
| 5,518,397 A | 5/1996 | Andreiko et al. | |
| 5,533,895 A | 7/1996 | Andreiko et al. | |
| 5,536,169 A | 7/1996 | Yousefian | |
| 5,562,448 A | 10/1996 | Mushabac | |
| 5,587,912 A | 12/1996 | Anderson et al. | |
| 5,605,459 A | 2/1997 | Kuroda et al. | |
| 5,607,305 A | 3/1997 | Anderson et al. | |
| 5,683,243 A | 11/1997 | Andreiko et al. | |
| 5,692,894 A | 12/1997 | Schwartz et al. | |
| 5,759,039 A | 6/1998 | Kunstadter et al. | |
| 5,829,980 A | 11/1998 | Sheridan et al. | |
| 5,934,907 A * | 8/1999 | Marshall ........................ 433/181 |

(Continued)

FOREIGN PATENT DOCUMENTS

DE 0837288 7/1949

(Continued)

*Primary Examiner* — Sunil K Singh
(74) *Attorney, Agent, or Firm* — Douglas J. Huras; David A. Zdurne; Leana Levin

(57) ABSTRACT

A pontic (10) having a prefabricated notch, channel or slot (11) to physically engage and ensure a secure mechanical lock with the dental appliance (30). The invention also pertains to a method of fabricating a dental appliance (30) and a kit for facilitating the same. The invention has particular application to thermoformed, removable appliances.

3 Claims, 3 Drawing Sheets

U.S. PATENT DOCUMENTS

| | | |
|---|---|---|
| 5,967,784 A | 10/1999 | Powers |
| 5,975,893 A | 11/1999 | Chishti et al. |
| 5,984,682 A | 11/1999 | Carlson |
| 6,015,289 A | 1/2000 | Andreiko et al. |
| 6,082,995 A | 7/2000 | Wise |
| 6,089,869 A | 7/2000 | Schwartz |
| 6,210,162 B1 | 4/2001 | Chishti et al. |
| 6,217,325 B1 | 4/2001 | Chishti et al. |
| 6,227,850 B1 | 5/2001 | Chishti et al. |
| 6,244,861 B1 | 6/2001 | Andreiko et al. |
| 6,293,790 B1 | 9/2001 | Hilliard |
| 6,299,440 B1 | 10/2001 | Phan et al. |
| 6,309,215 B1 | 10/2001 | Phan et al. |
| 6,318,994 B1 | 11/2001 | Chishti et al. |
| 6,345,984 B2 | 2/2002 | Karmker et al. |
| 6,368,109 B2 | 4/2002 | Lindquist |
| 6,371,759 B1 | 4/2002 | Schwartz |
| 6,382,979 B2 | 5/2002 | Lindquist |
| 6,386,864 B1 | 5/2002 | Kuo |
| 6,390,812 B1 | 5/2002 | Chishti et al. |
| 6,394,801 B2 | 5/2002 | Chishti et al. |
| 6,398,548 B1 | 6/2002 | Muhammad et al. |
| 6,406,292 B1 | 6/2002 | Chishti et al. |
| 6,409,504 B1 | 6/2002 | Jones et al. |
| 6,413,086 B1 | 7/2002 | Womack |
| 6,450,807 B1 | 9/2002 | Chishti et al. |
| 6,454,565 B2 | 9/2002 | Phan et al. |
| 6,457,972 B1 | 10/2002 | Chishti et al. |
| 6,463,344 B1 | 10/2002 | Pavloskaia et al. |
| 6,471,511 B1 | 10/2002 | Chishti et al. |
| 6,485,298 B2 | 11/2002 | Chishti et al. |
| 6,488,499 B1 | 12/2002 | Miller |
| 6,499,995 B1 | 12/2002 | Schwartz |
| 6,514,074 B1 | 2/2003 | Chishti et al. |
| 6,524,101 B1 | 2/2003 | Phan et al. |
| 6,554,611 B2 | 4/2003 | Chishti et al. |
| 6,572,372 B1 * | 6/2003 | Phan et al. ............ 433/6 |
| 6,582,227 B2 | 6/2003 | Phan et al. |
| 6,599,125 B1 | 7/2003 | Freilich et al. |
| 6,602,070 B2 | 8/2003 | Miller et al. |
| 6,602,076 B2 | 8/2003 | Adams |
| 6,607,382 B1 | 8/2003 | Kuo et al. |
| 6,621,491 B1 | 9/2003 | Baumrind et al. |
| 6,626,666 B2 | 9/2003 | Chishti et al. |
| 6,629,840 B2 | 10/2003 | Chishti et al. |
| 6,633,789 B1 | 10/2003 | Nikolskiy et al. |
| 6,665,570 B2 | 12/2003 | Pavloskaia et al. |
| 6,682,344 B1 | 1/2004 | Stockstill |
| 6,682,346 B2 | 1/2004 | Chishti et al. |
| 6,685,469 B2 | 2/2004 | Chishti et al. |
| 6,685,470 B2 | 2/2004 | Chishti et al. |
| 6,688,886 B2 | 2/2004 | Hughes et al. |
| 6,694,212 B1 | 2/2004 | Kennedy |
| 6,699,037 B2 | 3/2004 | Chishti et al. |
| 6,702,575 B2 | 3/2004 | Hilliard et al. |
| 6,705,861 B2 | 3/2004 | Chishti et al. |
| 6,705,863 B2 | 3/2004 | Phan et al. |
| 6,729,876 B2 | 5/2004 | Chishti et al. |
| 6,790,035 B2 | 9/2004 | Tricca et al. |
| 2002/0006597 A1 | 1/2002 | Andreiko et al. |
| 2003/0190575 A1 | 10/2003 | Hilliard et al. |
| 2004/0038171 A1 | 2/2004 | Jacobs et al. |
| 2004/0081935 A1 | 4/2004 | Stockstill |
| 2005/0048433 A1 | 3/2005 | Hilliard |
| 2005/0064358 A1 | 3/2005 | Nicozisis |
| 2005/0202369 A1 * | 9/2005 | Lee ............................ 433/180 |

FOREIGN PATENT DOCUMENTS

| | | |
|---|---|---|
| DE | 2063753 | 8/1972 |
| DE | 2257941 | 8/1974 |
| FR | 2763238 A1 | 11/1998 |
| WO | 9903357 A1 | 1/1999 |
| WO | 9942055 A1 | 8/1999 |
| WO | 03001835 A1 | 1/2003 |
| WO | 03082137 A1 | 10/2003 |
| WO | 03084422 A1 | 10/2003 |
| WO | 2005-023129 A2 | 3/2005 |
| WO | 2005064358 A1 | 7/2005 |
| WO | 2006031906 A2 | 3/2006 |

* cited by examiner

NOTCHED PONTIC AND SYSTEM FOR FABRICATING DENTAL APPLIANCE FOR USE THEREWITH

RELATED APPLICATIONS

This application is a U.S. non-provisional application which claims benefit from U.S. non-provisional application Ser. No. 11/226,763 filed Sep. 14, 2005 which claims the priority benefit from U.S. Provisional Application No. 60/609,660 filed Sep. 14, 2004.

TECHNICAL BACKGROUND

The present invention is a temporary bridge as used with a dental appliance such as a retainer. More particularly, the invention relates to a pontic having a prefabricated channel or slot, such as a lingual channel therein, helping to ensure a secure mechanical lock with the dental appliance. The invention also pertains to a method of fabricating a dental appliance and a kit for facilitating the same. The invention has particular application to removable appliances.

BACKGROUND OF THE INVENTION

Dental appliances are used for a multitude of dental operative procedures. For example, a suitable plastic tray can be used in an orthodontic procedure to move teeth, and can also be used in a post-procedure to retain the teeth in the desired position. Such trays are known and are formed from plastic materials such as Essix C+ or ACE, each available from Raintree Essix of Metairie, La.

These trays are often thermoformed over a model of the patient's dentition. If the patient is missing a tooth, then the void in the resulting dental model will cause problems with the subsequent thermoforming operation. Further, because dental appliances such as tooth movement trays and retainers are used with ongoing dental procedures, the patient often cannot benefit from the well established dental procedures for restoring such deficiencies. That is, until the treatment is over, the patient often cannot get a new bridge, crown or other restorative. During the treatment period then, the patient must tolerate the dental deficiency. One solution to helping alleviate the patient's problem has been to provide temporary bridges and the like using appliances known as flippers. A flipper is a temporary artificial tooth that is attached with either a wire or a plastic piece that fits in the roof of the mouth. This is uncomfortable at best although it may be aesthetically acceptable.

Another solution which is adapted for use with removable appliances such as tooth movement trays and retainers has been to affix a temporary crown into the appliance itself in the area of the patient's missing tooth. Thus when the patient wears the appliance, the temporary pontic is positioned in the missing tooth space and appears normal to a casual observer.

Further still it has been the practice to actually affix the pontic to the model of the patient's dentition, such that when the appliance is thermoformed over the model, the pontic is embedded in the resulting appliance. This also helps to overcome the problems associated with trying to thermoform an appliance over a model with a missing tooth. To help secure the pontic to the appliance, it has also been the practice to cut a channel in the pontic to help mechanically lock the pontic into the plastic during thermoforming. Such procedures are time consuming for the dental practitioner. A need exists therefore for a preformed pontic or set of pontics for use as temporary bridges with dental appliances. It should be simple and rapid for the dental practitioner to employ such pontics in the fabrication of the dental appliance.

SUMMARY OF THE INVENTION

There is provided according to the invention, a thermoformed dental appliance constructed by making an impression of a patient's dentition, constructing a dental impression cast from said impression, providing a pontic having a notch pre-formed therein and fitting same to the edentulous area of the cast, temporarily adhering the pontic to the cast, thermoforming a plastic sheet over the cast to form the appliance, while allowing the pontic to dislodge from the cast and mechanically lock into the appliance. The pontic may be selected from a plurality of pontics having different color, hue and or brightness characteristics or combinations thereof. The plurality of pontics may also have different sizes and shapes.

There is also provided according to the invention a method of constructing a dental appliance incorporating a pontic, comprising the steps of
 a) making an impression of a patient's dentition;
 b) constructing a dental impression cast from said impression;
 c) providing a pontic having a notch pre-formed therein and fitting same to the edentulous area of the cast, temporarily adhering the pontic to the cast;
thermoforming a plastic sheet over the cast to form the appliance, while allowing the pontic to dislodge from the cast and mechanically lock into the appliance. The pontic may be selected from a plurality of pontics having different color, hue and or brightness characteristics or combinations thereof. The plurality of pontics may also have different sizes and shapes.

Another method according to the invention for manufacturing a pontic comprises the steps of:
 a) providing an injection mold having a cavity for forming said pontic;
 b) providing notch forming means in associated with said injection mold;
injecting thermoplastic into said mold and allowing same to cure, so as to form a pontic having a notch formed therein. A plurality of such pontics may be provided having different color, hue and or brightness characteristics or combinations thereof. The plurality of pontics may also have different sizes and shapes.

According to a still further inventive method, a method of building a dental bridge incorporating a pontic, comprises the steps of:
 a) forming a plurality of pontics of various sizes, shapes and colors;
 b) forming a mounting notch in each of said pontics in one or more locations on said pontic, providing a variety of pontics having mounting notches formed therein;
providing said pontics to a dental caregiver so as to provide said dental caregiver with a greater selection so that the dental caregiver has a greater statistical probability of utilizing a pontic comprising a satisfactory match to the patients teeth, with nominal customization and no notch preparation required. The pontic may be selected from a plurality of pontics having different color, hue and or brightness characteristics or combinations thereof. The plurality of pontics may also have different sizes and shapes.

There is also provided according to the present invention, a kit for fabricating a dental appliance having at least one pontic affixed thereto, comprising a plurality of pontics of various size, shape, color, hue, brightness or combinations thereof; each said pontic of said plurality having a notch in one or more locations thereon.

PREFERRED EMBODIMENTS FOR CARRYING OUT THE INVENTION

Figure 5:
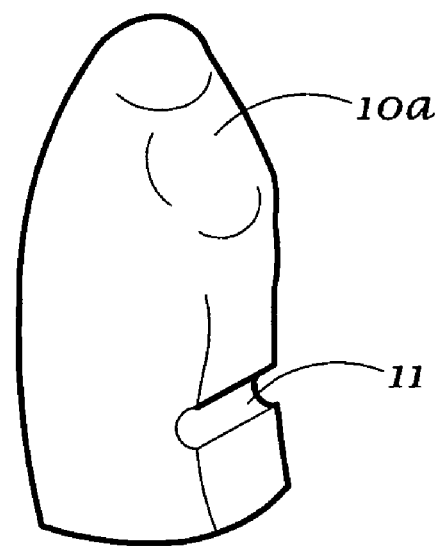
FIG. 5 is a perspective view of an exemplary pontic according to the invention.

The present invention relates to dental appliances such as temporary anterior bridges or the like, and particularly a dental appliance utilizing a modular, customizable assembly including one or more pontics, each having the mounting notch pre-formed therein during manufacture. As used herein, "notch" means any channel, cut, scrape, gouge, etch, trench, void or other indentation, whether of regular or irregular shape and size, without limitation. The pontic according to the invention may have one of more such notches placed at one or more locations thereon. As an example, the pontic as shown in FIG. 5 is provided with a notch in the form of a lingual channel. Because other notch shapes, locations and numbers thereof on a given pontic may vary, all such variations have not been shown on the drawings and the notch as shown is considered to be representative of all such notches.

The preferred embodiment of the present invention thereby provides a temporary anterior bridge which requires less time and effort to fabricate, and is more economical in implementation. While the invention has application to any dental appliance, it is particularly suited for use with removable appliances thermoformed from plastic sheet materials. The notch 11 as described herein serves to physically engage the appliance during for example, the thermoforming of the appliance, and helps to secure the pontic to the appliance thereby formed.

Dental care providers have long been making temporary anterior bridges to simulate missing teeth in patients, for the patient to wear until a permanent solution can be provided. For this purpose, an off-the-shelf pontic, or artificial tooth, is employed to form a fixed partial denture or thermoplastic slip over appliance to replace the lost natural tooth, restore its function, and to occupy the space previously occupied by the natural crown. In the past, the pontic had to be prepared by notching same to facilitate securing it to the appliance, which requires additional steps which had to be performed by the dental caregiver.

Figure 6:
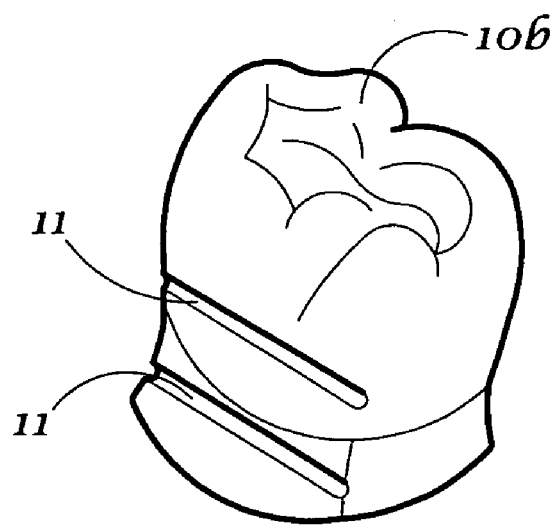
FIG. 6 is a perspective view of another exemplary pontic according to the invention.

Unlike the prior art, the present invention provides a ready-made pontic 10 which incorporates a notch 11 (FIGS. 5 and 6) formed therein during manufacture, so as to dispense with the necessity of manually forming the required notches during preparation of the bridge for the patient. FIG. 5 shows a representation of an anterior pontic 10a while FIG. 6 is an example of a posterior pontic 10b. It is understood that the term pontic refers to any portion of a bridge or other dental restoration that takes the place of a missing natural tooth or portion thereof.

A selection of pontics 10, 10a and 10b is thereby formed of various sizes and colors, hues, brightness or combinations thereof, already having a notch 11 or trench formed in the outer surface of the pontic. In the case of thermoplastic slip on, that is removable appliances, the notch may preferably be formed on the lingual surface, as will be shown on the present drawings.

During manufacture, each pontic is formed by injection molding or the like, which molds may include means to form the notch or ridge to facilitate securing the pontic to the appliance. A variety of sized, shaped, and colored pontics are provided for use by the dental care provider in his/her practice to best match the missing tooth or teeth of the patient.

In practice, an impression is made of the patient, and working cast is then formed for use in fabricating the appliance.

The attached figures illustrate utilizing the pontic 10 with a pre-formed notch 11 (FIG. 3) on the lingual surface of said pontic, for fabricating a slip-on thermoplastic appliance.

Figure 1:
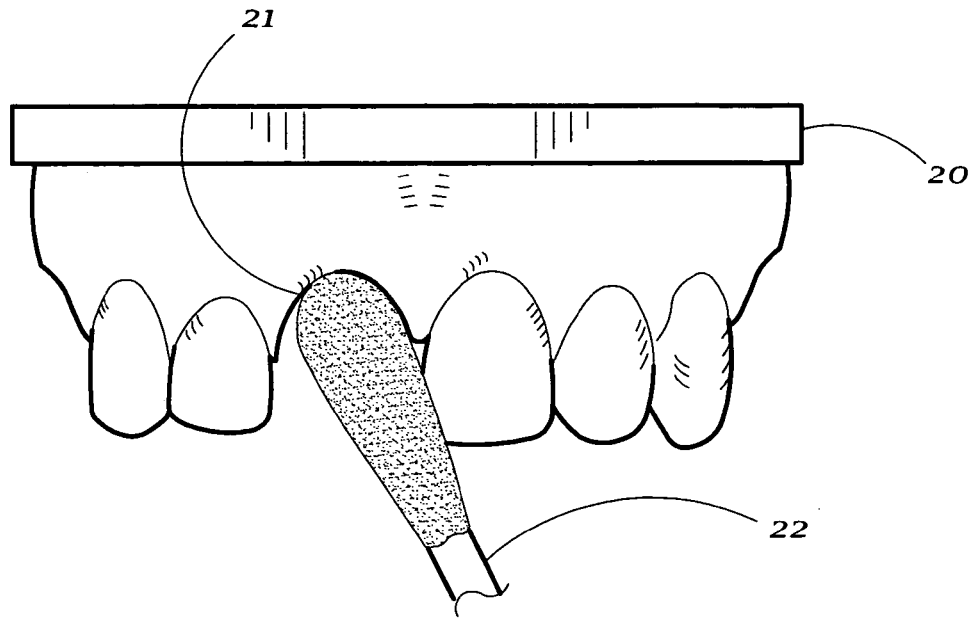
FIG. 1 is a front perspective view of a model of a patient's upper dental arch and having a missing tooth thereon.

In the example illustrated in FIG. 1 of the drawings, a separating medium is applied to the edentulous alveolar ridge area 21 of a dental cast 20 using any conventional means such as swab 22.

Figure 2:
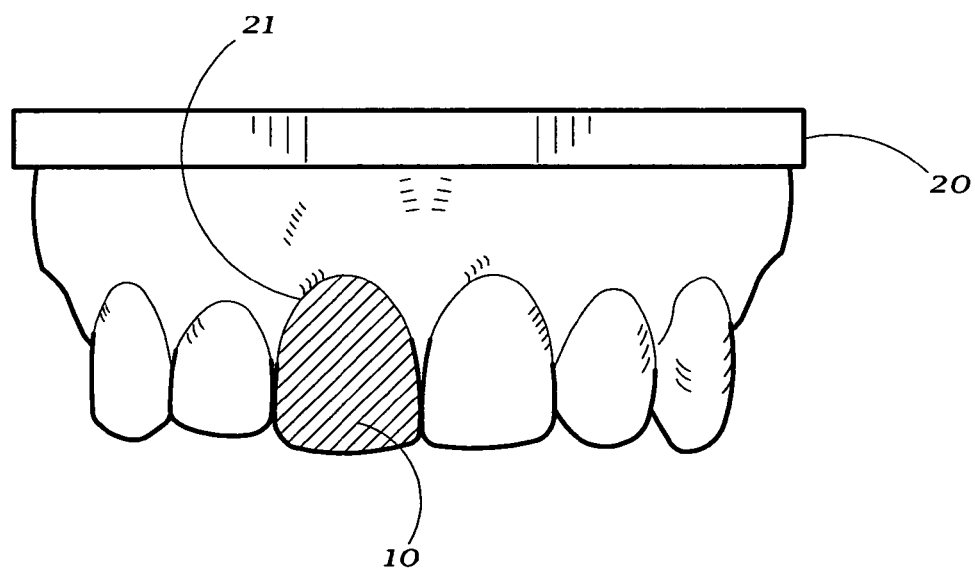
FIG. 2 is a front perspective view of a model as in FIG. 1 showing a temporary pontic according to the invention affixed to the model in the area of the patient's missing tooth.

Referring to FIG. 2, a suitable pontic 10 is chosen by the dental care provider to provide the appropriate size and color, hue and/or brightness, and is fitted into the edentulous area 21 of the cast 20. The base of the pontic 10 may have to be trimmed to approximate the ridge and provide a secure fitting.

Figure 3:
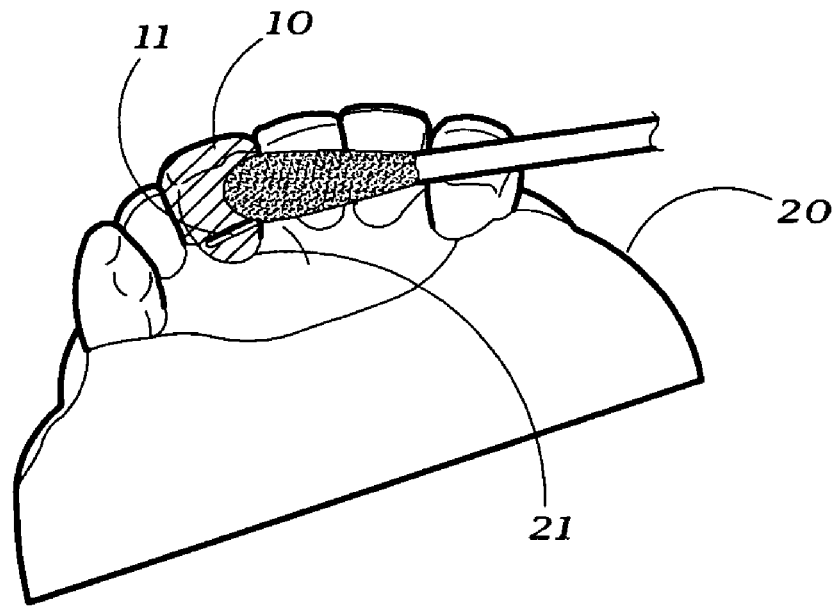
FIG. 3 shows a rear perspective view of the model of FIG. 2, showing the pontic being affixed to the model.

FIG. 3 illustrates a lingual view of the pontic fitted to the edentulous area 21 of the cast 20, with the pre-formed notch 11. The pontic 10 is then secured to the cast with quick-cured acrylic or any other conventional thermally compatible adhesive (not shown) for subsequent thermoforming, using any conventional means such as with swab 22. For aesthetic purposes, pink acrylic may be used in the gingival area.

Figure 4:
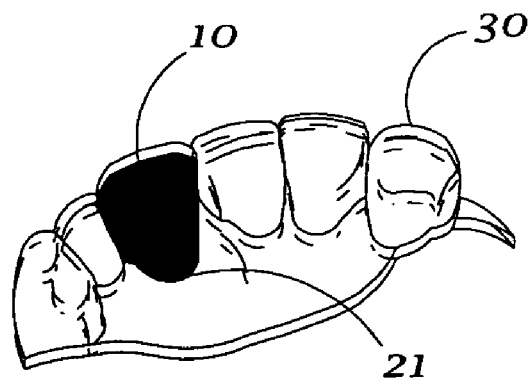
FIG. 4 shows the pontic of FIGS. 2 and 3 embedded and mechanically locked into a plastic tray retainer.

Once secured to the cast, a plastic sheet such as Essix C+, Essix A+ for children, or the like may be thermoformed over the cast utilizing an Essix brand vacuum thermoformer or the like over the thus prepared cast 20, resulting in the formation of dental tray appliance 30. Once thermoformed, the pontic 10 should dislodge from the cast 20 and mechanically lock into the appliance 30 as is depicted in FIG. 4. The appliance 30 may then be conventionally trimmed for a secure and comfortable fit.

By "mechanically lock" and such terms it is considered that the preformed notch serves to physically engage material from the plastic appliance in a manner that the physical interaction therebetween holds, grabs or otherwise secures the pontic to the appliance.

In order to facilitate the fabrication of a dental appliance such as tray 30 having a pontic 10 according to the present invention, the invention also provides a kit for fabricating the dental appliance. The kit includes a plurality of pontics as above of various size, shape, color, hue, brightness or combinations thereof as discussed hereinabove. Each pontic of the inventive plurality has a notch in one or more locations thereon, as also described hereinabove.

The inventive kit may also include a dental compound for temporarily affixing at least one of the pontics to the dental model. An example of such an affixing compound is a block-out compound such as Triad Gel available from DENTSPLY International of York, Pa. The material used to affix the pontic to the model should not be a permanent adhesive, but may be a reversible adhesive. The material preferably is able to withstand melting at the subsequent thermoforming temperature, has suitable strength to hold the pontic in place during such procedures but is easily removable such that once the tray is removed from the model the bond between the compound and the pontic is readily and easily broken. The kit may include for example, at least one pontic having a notch that is a lingual channel or any such shape, location or number of notches. The kit also preferably includes pontics in the shapes of upper and lower anterior and posterior teeth or combinations thereof.

It is reiterated that the pontic and its use in the above illustration is for exemplary purposes, and the notch location and configuration can vary depending upon the application and appliance used.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

The invention claimed is:

1. A method of constructing an orthodontic positioning appliance incorporating a pontic, comprising the steps of:
    a) making an impression of a patient's dentition;
    b) constructing a dental impression cast from said impression, the cast having an edentulous area;
    c) providing a pontic having a notch pre-formed therein;
    d) fitting the pontic having the notch pre-formed therein to the edentulous area of the cast;
    e) temporarily adhering the pontic to the cast;
    f) thermoforming a plastic sheet over the cast to form a plastic orthodontic positioning appliance, wherein a portion of the plastic sheet physically engages the pre-formed notch of the pontic to mechanically lock the pontic to the plastic orthontic postioning appliance; and
    g) removing the plastic orthodontic possition appliance with the mechanically locked pontic therein from the cast.

2. A method of constructing a an orthodontic positioning appliance incorporating a pontic, comprising the steps of:
    a) making an impression of a patient's dentition;
    b) constructing a dental impression cast from said impression, the cast having an edentulous area;
    c) providing a pontic having a notch pre-formed therein;
    d) fitting the pontic having the notch pre-formed therein to the edentulous area of the cast; and
    e) thermoforming a plastic sheet over the cast to form a plastic orthodontic positioning appliance, wherein a portion of the plastic sheet physically engages the pre-formed notch of the pontic to mechanically lock the pontic into the plastic orthodontic positioning appliance while allowing the pontic to dislodge from the cast; and
    (f) removing the plastic orthodontic positioning appliance with the mechanically locked pontic therein from the cast.

3. The method of claim 2, further comprising the step of temporarily adhering the pontic to the cast.

* * * * *